(12) United States Patent
Melechco Carvalho et al.

(10) Patent No.: US 8,067,242 B2
(45) Date of Patent: Nov. 29, 2011

(54) METHOD FOR METHYLMALONIC ACID DETEMINATION BASED ON ALKYLATIVE EXTRACTION ASSOCIATED TO LIQUID CHROMATOGRAPHY COUPLED TO MASS SPECTROMETRY

(76) Inventors: Valdemir Melechco Carvalho, São Paulo (BR); Fernando Kok, São Paulo (BR)

( * ) Notice: Subject to any disclaimer, the term of this patent is extended or adjusted under 35 U.S.C. 154(b) by 83 days.

(21) Appl. No.: 12/312,250
(22) PCT Filed: Nov. 5, 2007
(86) PCT No.: PCT/BR2007/000302
  § 371 (c)(1),
  (2), (4) Date: May 26, 2009
(87) PCT Pub. No.: WO2008/052299
  PCT Pub. Date: May 8, 2008

(65) Prior Publication Data
  US 2010/0304492 A1  Dec. 2, 2010

(30) Foreign Application Priority Data
  Nov. 3, 2006 (BR) ........................... 0605166

(51) Int. Cl.
  G01N 33/50   (2006.01)
  G01N 30/72   (2006.01)
  G01N 30/06   (2006.01)
  G01N 1/28    (2006.01)
(52) U.S. Cl. ............ 436/129; 436/43; 436/52; 436/127; 436/128; 436/161; 436/177; 436/178
(58) Field of Classification Search .................... 436/43, 436/52, 127–129, 161, 173–174, 177–178
  See application file for complete search history.

(56) References Cited

U.S. PATENT DOCUMENTS

| 4,990,458 | A  | * | 2/1991  | Rosenfeld ................... 436/174 |
| 5,457,055 | A  | * | 10/1995 | Allen et al. .................. 436/129 |
| 5,508,204 | A  | * | 4/1996  | Norman ........................ 436/161 |
| 5,658,800 | A  | * | 8/1997  | Lessard et al. ............... 436/178 |
| 2002/0019056 | A1 | * | 2/2002  | Shushan et al. ............... 436/129 |
| 2002/0142401 | A1 | * | 10/2002 | Santi et al. ..................... 435/76 |
| 2005/0164402 | A1 | * | 7/2005  | Belisle et al. ................. 436/174 |
| 2005/0165560 | A1 | * | 7/2005  | Kushnir et al. ................ 702/30 |
| 2006/0218990 | A1 | * | 10/2006 | Kawana ........................ 73/23.37 |
| 2009/0298117 | A1 | * | 12/2009 | Zhang et al. ................... 435/42 |

OTHER PUBLICATIONS

Gyllenhaal, O. et al, Journal of Chromatography 1976, 129, 295-302.*
Fogelqvist, E. et al, Journal of High Resolution Chromatography & Chromatography Communications 1980, 3, 568-574.*
Matchar, D. B. et al, Annals of Internal Medicine, 1987, 106, 707-710.*

(Continued)

*Primary Examiner* — Arlen Soderquist
(74) *Attorney, Agent, or Firm* — The Nath Law Group; Joshua B. Goldberg; Tanya E. Harkins

(57) ABSTRACT

The present invention relates to the determination of the presence of methylmalonic acid in biologic samples including the steps of methylmalonic extraction from the sample; derivatization of methylmalonic acid and use of mass spectrometry with negative mode atmospheric pressure chemical ionization to determine the presence of methymalonic acid throughthe formation of an ion of mass to charge ratio (m/z) 477. An additional objective of the present invention concerns diagnosis kits for determination of presence and quantification of methylmalonic acid based on the method mentioned before.

6 Claims, 8 Drawing Sheets

OTHER PUBLICATIONS

Montgomery, J. A. et al, Methods in Enzymology 1988, 166, 47-55.*
Hachey, D. L. et al, Analytical Chemistry 1991, 63, 919-923.*
Balazy, M., Journal of Biological Chemistry 1991, 266, 23561-23567.*
Kajita, M. et al, Journal of Chromatography 1993, 622, 263-268.*
Naritsin, D. B. et al, Analytical Chemistry 1995, 67, 863-870.*
Fitzsimmons, M. E. et al, Biochemistry 1995, 34, 4276-4286.*
Singh, G. et al, Analytical Chemistry 2000, 72, 3007-3013.*
Magera, M. J. et al, Clinical Chemistry 2000, 46, 1804-1810.*
Kushnir, M. M. et al, Clinical Chemistry 2001, 47, 1993-2002.*
Penttila, I. et al, Journal of Chromatography, Biomedical Applications 1985, 338, 265-272.*
Mills, G. A. et al, Biomedical and Environmental Mass Spectrometry 1988, 16, 259-261.*
Jemal, M. et al, Journal of Chromatography B 1998, 709, 233-241.*

* cited by examiner

METHOD FOR METHYLMALONIC ACID DETEMINATION BASED ON ALKYLATIVE EXTRACTION ASSOCIATED TO LIQUID CHROMATOGRAPHY COUPLED TO MASS SPECTROMETRY

This is a National Phase Application filed under 35 U.S.C. 371 as a national stage of PCT/BR2007/000302, with the filing date of Nov. 5, 2007, the entire content of which is hereby incorporated by reference in its entirety.

FIELD OF INVENTION

The present invention refers to a method for determining the presence of methylmalonic acid (MMA) in biologic samples and diagnosis kits based on it.

More specifically, the methodology refers to a new strategy for determining the presence of MMA on serum and other biological matrices through the combination of alkylative extraction with liquid chromatography coupled to mass spectrometry.

The method developed herein presents advantages on the sample preparation, higher sensitivity and elimination of the interference of succinic acid, a MMA isomer more abundant physiologically.

BACKGROUND OF THE INVENTION

Methylmalonic Acid (MMA)

MMA is a byproduct of metabolic route, which converts degradation products of specific amino acids, fatty acids of odd chain, cholesterol and thimine into succinic acid, which is, in turn, incorporated into Krebs cycle (FIG. 1)[1]. MMA does not have known biologic function, and it is usually presented at very low levels. However, genetic disorders which result on lack or reduction of activity of several enzymes of this route result in increased excretion of MMA, turning it into a marker of a set of hereditary diseases collectively known as methylmalonic acidemias.

However, the main reason for MMA to gain clinic importance is its close relation with cobalamin or $B_{12}$ vitamin. The conversion of methylmalonyl-CoA into succinyl-CoA is one of the two cobalamin-dependent reactions shown in mammals. As a consequence, the changes on cobalamin levels reflect directly on MMA levels. There is an accumulation of evidences indicating that MMA is the best marker of cobalamin levels, even better than the appropriate dosage of cobalamin in blood[3,4,5]. This is explained by the following reasons: the serum is levels of cobalamin do not necessarily reflect its intracellular concentration, the cobalamin quantification methods that are based on radioimmunoassay have low specificity, MMA is more stable than cobalamin in blood, and the reduction of cobalamin levels result in the increase of MMA levels which makes its dosage easier.

Despite the high potential of MMA use in clinical chemistry, its quantification is not still widely used due to technical difficulties.

The Challenge of the Low Molecular Weight Organic Acids Analysis on Biologic Matrices Although they are very simple in structure, the analysis of low molecular weight organic acids in biologic matrices is a very complex task. The quantification of methylmalonic acid (MMA) in serum is a good example of difficulties found on the determination of carboxylic acids of low molecular weight in biologic samples. The greater difficulties arise from its low endogenous concentration and the interference of other organic acids of low molecular weight in biologic samples, especially succinic acid, an isomer present in a) physiologic concentrations about 50 times higher than MMA.

Currently, the most used method for MMA identification and quantification is gas chromatography coupled to mass spectrometry (GC-MS). In spite of the good performance of this technique, it demands very complex procedures for the is extraction of analytes and derivatization, and long chromatographic separations. Several sample extraction strategies have already been described using methods such as strong ion exchange chromatography[6], liquid-liquid extraction[7] and the combination of liquid-liquid extraction with high performance liquid chromatography[8]. Likewise, several derivatization strategies have already been used as sterification with cyclohexane/HCl[6], silylation[3,9] and acylation with ethylchloroformate[6]. Besides the time consuming procedures of sample preparation and derivatization, the CG-MS analysis also demands long chromatographic separations to resolve structurally related compounds.

With approach of liquid chromatography coupled to mass spectrometry (LC/MS), the development of methods, which simplify this type of analysis was expected. In theory, liquid chromatography coupled to mass spectrometry with electrospray ionization on negative mode (ESI-LC/MS) could directly analyze low molecular weight organic acids from solution, since those compounds are polar and easily ionizable. But, in practice, this is virtually impossible in this range of molecular mass due to the interference from other compounds and even from the mobile phase. Thus, methodologies for analyte extraction and derivatization are still necessary and sample preparation step has become the most limiting step on the process.

Until now, two methods using LC-MS/MS have been described for MMA analysis on serum and urine[10,11]. Both of them used a similar strategy: butanolic HCl derivatization and detection of dibutylic esters by LC-MS/MS with positive mode electrospray ionization. One of the limitations of these methods is the potential interference of succinic acid, since it is also converted into an isomeric derivative, which produces spectra with similar masses. In order to solve this limitation and reduce the potential interference of succinic acid in the MMA quantification, Magera et al[10] have chromatographically resolved MMA from succinic acid derivatives. Kushnir et al have applied a data mathematic processing after the acquisition based on the difference in mass transition ratios for the determination of MMA concentration on the peak co-eluted with succinic acid. Although, this latter method represents a considerable advance compared to the previous ones, it also has several steps for sample preparation such as two cycles of evaporation, reconstitutions and tubes transferences. The second method was filed at "United States Patent and Trademark Office" (Pub. No: US 2002/0019056 A1). Although they show great simplicity comparing to methods based on GC-MS, they also demand long procedures for sample preparation. The development of more simple analytical methodologies is especially important on clinic environment where it is usually essential the acquisition of results on short periods and simple enough to not demand high level of technical expertise.

The methods as previously described also show the inconvenient of using 0.5 mL of sample. The sample volume reduction without loss of necessary sensitivity is especially important on this type of analysis since it is usually carried out on pediatric samples.

Another not-reached requirement by methodologies previously published is the specificity in relation to succinic acid, which is a MMA isomer present on very high physiologic levels. It would be important to reduce or eliminate the interference from this metabolite.

Thus, according to the knowledge presented from the state of the art, it would be interesting to develop a MMA identification and quantification process, which does not demand labourious procedures for the analytes extraction, complex derivatizations and long chromatographic separations. As well as, it would be interesting the development of detection kits, which eliminate steps of sample preparation, such as evaporation cycles, reconstitutions and transference from tubes to tubes. In addition, it would be important to precisely quantify the MMA in the presence of interferents such as succinic acid and using samples with reduced volumes to allow its quantification in pediatric samples.

BRIEF DESCRIPTION OF THE INVENTION

Considering the limitations shown by the methods presented on the state of the art and in the search of the elimination of deficiencies previously described, the present invention shows a new method for determination of the presence of methylmalonic acid (MMA) in biologic matrices and diagnosis kits based on it, able to use the MMA as marker of hereditary diseases collectively known as methylmalonic acidemias, as indicator of cobalamin levels, or even in other uses where the MMA analysis would be interesting.

More specifically, the methodology refers to the determination of MMA in biologic samples, especially serum and urine, through the combination of alkylative extraction followed by liquid chromatography coupled to mass spectrometry.

The present invention shows, more specifically, in its first embodiment, a methodology of MMA presence identification and quantification and in its second embodiment, diagnosis kits that use this method. The method of the present invention uses techniques such as pentafluorobenzylation derivatization that allows the detection through atmospheric pressure chemical ionization (APCI) or through electrons capture atmospheric pressure chemical ionization (ECAPI). Both processes result in the formation of negative ions, which can be detected with high sensitivity. For MMA specifically, the ionization process leads to the formation of two major species: one resulting from ECAPI with a loss of pentafluorobenzyl group and the other resulting from deprotonation. The ion produced from deprotonation presents a peak of mass/charge ratio (m/z) 477, which is totally absent on the succinic acid pentafluorobenzyl derivative mass spectrum.

As the formation of deprotonated molecule is unique for MMA, the method allows the isomeric discrimination between MMA and succinic acid. Consequently, the technique can be used for the determination of MMA presence without succinic acid interference.

Since it uses alkylative extraction and process optimized parameters, the sample preparation on this method is simpler and quicker, resulting in a very suitable method for the clinical chemistry laboratories routine. Additionally, the sample volume required is much lower, which turns it very appropriate to pediatric samples.

DETAILED DESCRIPTION OF THE INVENTION

Figure 1:
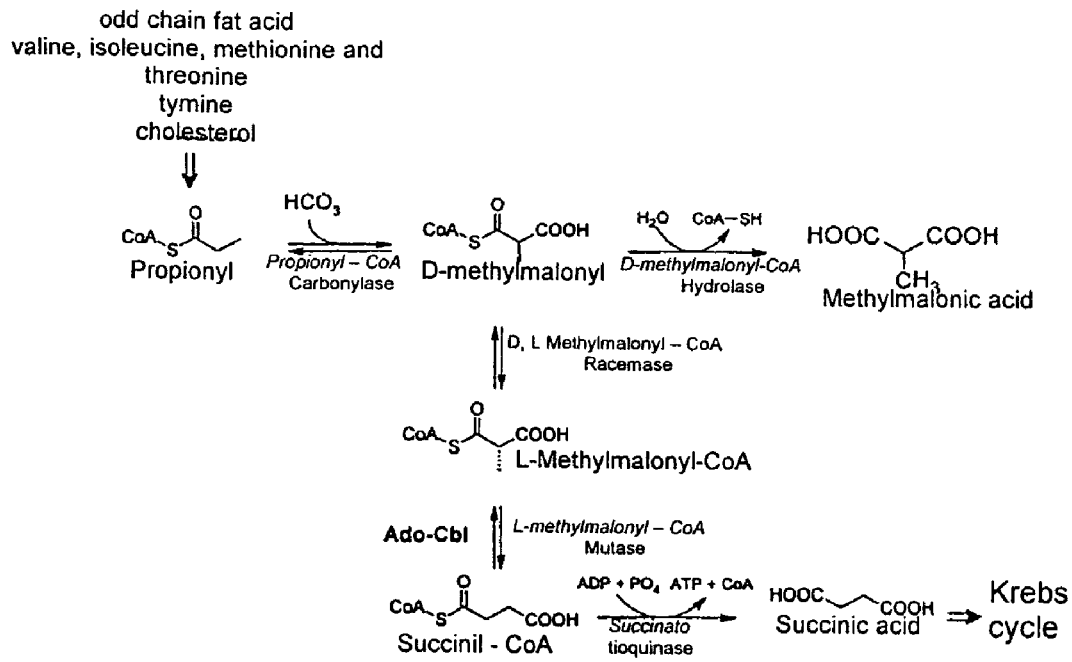
FIG. 1 shows metabolic routes involved on methylmalonic acid production.

In other words, the method of the present invention uses pentafluorobenzilation which is a very efficient derivatization process and allows the detection through electron capture on chemical ionization at atmospheric pressure (ECAPCI). When it is carried out on APCI-ionization source the electric discharge produced by the corona needly of APCI source acts as an electron source. In this process, the loss of a PFB group occurs with the production of negative ion, which can be detected with high sensitivity. The ion produced from ECAPCI was observed at m/z 297, however, the most abundant peak was detected at m/z 477. This peak was attributed to the ion produced by deprotonation of MMA-PFB$_2$ derivative. One of the major advantages of this method over the ones of the state of the art is exactly the presence of this peak, since succinic acid is not able to form this ion. This phenomenon could be explained due to the strong inductive effect of two PFB groups which are electrons withdrawing groups, concentrated on tertiary carbon of MMA-PFB$_2$ molecule. Such effect increases the acidity of this carbon, favoring its ionization by deprotonation rather than by dissociative electron capture, which is the unique possible mechanism for succinic acid derivative. Since the deprotonated molecule formation is unique for MMA, the method allows the isomeric discrimination between MMA and succinic acid. Consequently, this technique can be used for MMA quantification without interference of succinic acid.

Another clear advantage of the present method is the use of a very simple sample preparation. The analyte is transferred from the aqueous phase to the organic phase by the action of a phase-transfer reagent as tetrabutylammonium. Once at the organic phase, the anion reacts with an alkylative reagent such as pentafluorobenzyl bromide, and it is converted into a disubstituted derivative. In order to reach the necessary efficacy for the detection of low concentrations in which the MMA is present in biological matrices, it was necessary to optimize all the reaction parameters. The result of those studies was the acquisition of a very simple procedure of sample preparation which demands, as an example, reduced volumes as 50 µl of serum. The use of APCI ionization technique, which is very robust and less sensitive to the ionic suppression than the electrospray, allowed the direct analysis of the extract.

The new developed strategy resulted in a simple, quick and low-cost method, which is very appropriate to high volume testing. The detection by negative mode APCI resulted in excellent sensitivity and requiring low volumes of serum samples, and allows the distinction between the MMA and succinic acid isomeric compounds. Finally, the method can be adjusted for MMA analysis in different biologic matrices, such as plasma, urine, total blood, cerebrospinal fluid, saliva and other biologic fluids that has MMA measurable concentrations. Also, the method can be adjusted for the quantification and determination of other organic acids.

EXAMPLE 1

Reagents

The illustrative examples of diagnosis kits and methodology of the present invention show as non-limiting way the following reagents that belong to the state of the art subject to be used: methylmalonic acid and 2,3,4,5,6-pentafluorobenzyl bromide optionally obtained from Fluka Chemie GmbH (Buchs, Switzerland); methyl-$d_3$-malonic acid, from CDN Isotopes (Pointe-Claire, Canada); acetonitrile and dichloromethane, from Tedia (Fairfield, USA); triethylamine and dimethylsulfoxide, from Sigma Chemical CO (St. Louis, USA) and tetrabutylammonium hydrogen sulfate, from Vetec Química Fina Ltda (R10 de Janeiro, Brazil).

EXAMPLE 2

Instrumentation

The analysis of illustrative examples shown below were carried out with LC-MS/MS system composed by a tandem mass spectrometer Quattro Micro (Water/Micromass, Manchester, United Kingdom) equipped with an atmospheric pressure chemical ionization probe operating at negative mode, a HP 1050 sampler (Agilent Palo Alto USA) and HPLC system Shimadzu with two LC-10Atvp pumps (Shimadzu, Kyoto, Japan). The data acquisition and control of all system components were performed by MassLynx 4.0 program (Water/Micromass, Manchester, United Kingdom).

Analysis by Direct Infusion on the Spectrometry Ionization Source

The analysis by mass spectrometry on scan mode ("full scan" and "daughter scan") was performed through direct infusion of derivatives in acetonitrile/water (1:1) through a pump syringe integrated to the spectrometer. The spectrometer acquisition parameters such as ionization source voltages, probe and source temperatures, gas flow and collision energy were adjusted in order to maximize the signals of ions of interest. The analyses on the full scan mode were performed at the mass interval of 250-500 Th. The analyses on daughter scan mode were performed at the interval of 100-500 Th.

Analysis by Liquid Chromatography Coupled to Tandem Mass Spectrometry (LC-MS/MS)

The chromatographic analysis was performed using a Synergi-MaxRP 4µ 50×2 mm column (Phenomenex, Torrance, USA) eluted with 70% acetonitrile at 0.4 mL/min. The acquisition was performed by multiple reactions monitoring mode using the mass transition 477>231 and 477>279 for the detection of PFB derivative of MMA and 480>234 and 480>281 for detection of deuterated internal standard derivative (AMM-$d_3$).

EXAMPLE 3

Preparation of Solutions and Calibrators

Primary standard stock (S0)—1 mg/mL Methylmalonic Acid Solution (8.468 mmol/L)

10 mg of methylmalonic-$d_3$ acid and add to a 100 mL-volumetric flask, a milli-Q water volume for 100 mL (concentration 0.847 mmol/L). Storage: −25° to −10° C. Validity: one month.

Secondary Stock Solutions (S1)

Dilute th primary stock solution (S0) preferably according to table 1 below to obtain the following MMA solutions in water: 0.02, 0.04, 0.08, 0.15 and 0.30 mmol/L. Storage: −25° to −10° C. Validity: one month.

TABLE 1

| S1 (mmol/L) | S0 (µL) | Água mQ (µL) |
| --- | --- | --- |
| 0.02 | 118 | 4882 |
| 0.04 | 236 | 4764 |
| 0.08 | 472 | 4528 |
| 0.15 | 885 | 4115 |
| 0.30 | 1771 | 3229 |

Calibration Curve

Dilute the S1 stock solution in pool of serum dialyzed against PBS for one week, according to table 2, below, to obtain the calibrators on the following concentrations: 0.2, 0.4, 0.8, 1.5 and 3.0 µmol/L. Perform aliquots of 50 µL of each solution on Sarstedt tubes with screw cap. Identify the tubes and store them at freezer. Storage: −25° to −10° C. Validity: three years.

TABLE 2

| | S1 (mmol/L) | S1 (µL) | Serum dialysed (µL) | Final Concentration (µmol/L) |
| --- | --- | --- | --- | --- |
| CC1 | 0.02 | 10 | 990 | 0.2 |
| CC2 | 0.04 | 10 | 990 | 0.4 |
| CC3 | 0.08 | 10 | 990 | 0.8 |
| CC4 | 0.15 | 10 | 990 | 1.5 |
| CC5 | 0.3 | 10 | 990 | 3.0 |

EXAMPLE 4

Preparation of Methylmalonic and Succinic Acids Derivatives

The methylmalonic and succinic acids pentafluorobenzyl derivatives were prepared mixing 2 mg (16.94 µmol) of each acid previously dissolved in 2 mL of acetonitrile with 200 µL of 7% pentafluorobenzyl bromide in acetonitrile (24.192 mg, 46.35 µmol) and 20 µL of triethylamine. The tubes were incubated at 65° C. for 2 hours. The solvent was completely removed on TurboVap LV (Caliper LifeSciences, Hopkinton, Mass.) and the residue was dissolved in 2 mL of acetonitrile.

EXAMPLE 5

Alkylative Extraction Reaction

Optimization of Alkylative Extraction Conditions

Figure 2:
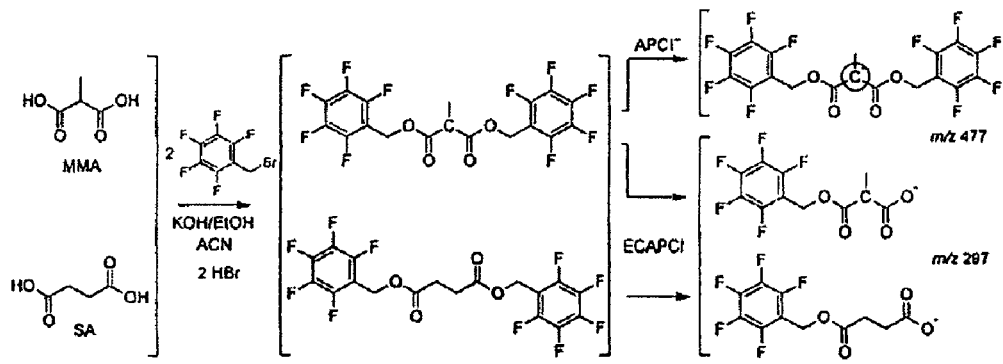
FIG. 2 represents the derivatization reaction of methylmalonic and succinic acids and their characteristic ions produced by negative APCI.

The reactions of derivatization of methylmalonic and succinic acids are shown in FIG. 2. The effects in the yield of derivative formation from MMA 100 µmol/L standard solution using different solvents, pHs, reaction temperatures, reagents concentration and reaction times were analyzed. The yields were calculated by relative responses or peak areas ratio between analyte and deuterated internal standard. To evaluate the effect of the different solvents in the reaction yield, studies were performed using the derivatization reaction in each one of the respective solvents: hexane, cyclohexane, iso-octane, ethyl ether, ethyl acetate, chlorobutane, trichloromethane and dichloromethane. To optimize the concentration of alkylating reagent, it was studied PFBBr concentrations from 0.05 to 2 mol/L. The effect of transfer-phase reagent concentration was evaluated testing tetrabutylammonium concentrations in the range of 0.05 to 0.8 mol/L. In order to establish the most efficient pH for derivatization reaction, TBA-HS/trimethylamine solutions were prepared on interval of pHs from 7 to 10 with increments of 1 unit. Temperatures from 40 to 90° C. with increments of 10° C. were tested. A second optimization cycle was performed using a pool of serum with 10 µmol/L of MMA and testing the PFBBr concentrations in the interval of 0.5-2 mol/L, TBA-HS/trimethylamine in interval of 0.2-0.8 mol/L and pH in the interval of 8-10 with increments of 0.5 units. Finally, the time of reaction was analyzed in the interval from 20 to minutes.

Standard Procedure for Sample Alkylative Extraction

After the reaction conditions optimization, the derivatization standard procedure was established. Aliquots of 50 µl of sample, calibration and quality control standards are transferred to 1.5 mL Sarstedt polypropylene microtubes with screw lid. Then 10 µL of internal standard is added (MMA-$d_3$, 100 µmol/L), 50 µL of TBA-HS/TEA buffer and 400 µL of derivatizing solution (0.1 mol/L PFBBr in dichloromethane) in each tube. The tubes are incubated in Thermomixer at 85° C. and 1400 rpm for one hour under hood with exhaustion. The tubes are centrifuged for 5 minutes at 13000 rpm, the lower phase is transferred to chromatographic vials and 50 µL of DMSO are added to each tube. The extract remains stable up to 48 hours.

EXAMPLE 6

Figure 3:
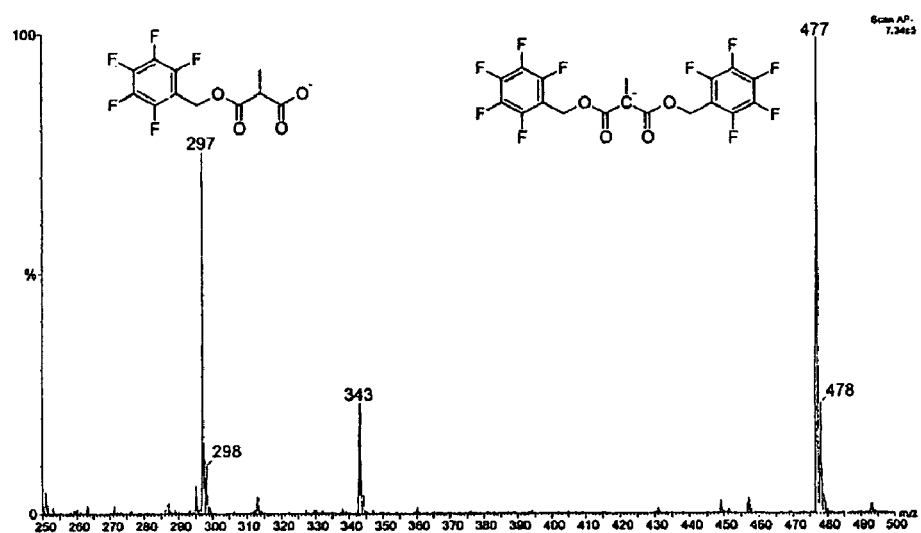
FIG. 3 shows MMA-PFB$_2$ derivative mass spectrum through negative APCI and proposed structures for m/z 477 and 297 peaks.

Results Obtained From Analysis of PFB Derivatives of Methylmalonic and Succinic Acids by Mass Spectrometry with Ionization by APCI on Negative Mode The mass spectrometry analysis with ionization by APCI on negative mode of MMA-PFB derivative has shown a spectrum with main peak of m/z 477 and two other less intense peaks at m/z 343 and 297. (FIG. 3).

The peak m/z 477 shows 1 Th less than the is expected mass for disubstituted derivative resulted from alkylation by PFBBr on the two MMA carboxyl groups. Consequently this ion would be generated by the deprotonation of disubstituted derivative (MMA-$PFB_2$). The peak at m/z 297 could be attributed to the MMA deprotonated monosubstituted derivative or the fragment produced after ionization by electron capture and loss of one PFB group.

Figure 4:
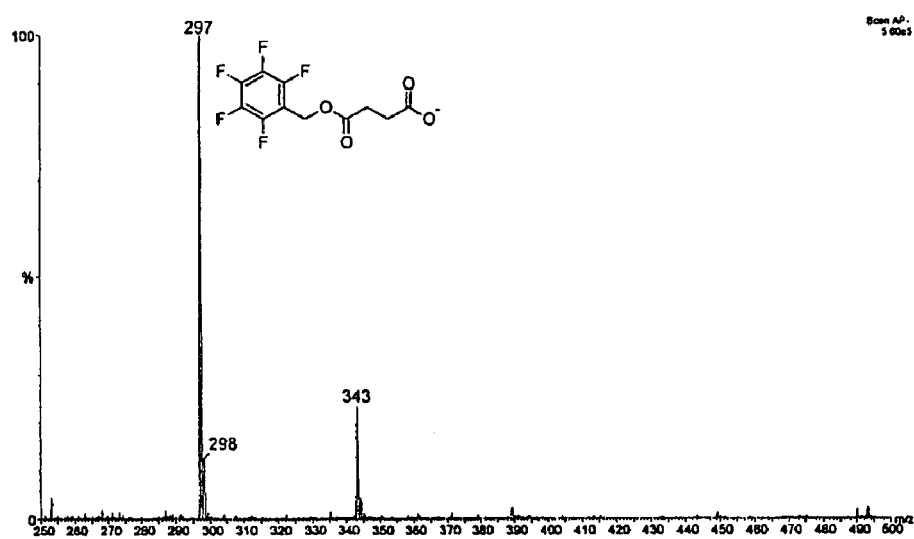
FIG. 4 shows succinic acid-PFB$_2$ derivative mass spectrum through APCI on negative mode and proposed structure of m/z 297 peak.

The succinic acid-PFB derivative analyzed at identical mass spectrometry conditions has shown only peaks at m/z 297 and 343 (FIG. 4). The difference on spectra shown by the derivatives of two isomeric acids indicated the presence of two different ionization mechanisms.

Figure 5:
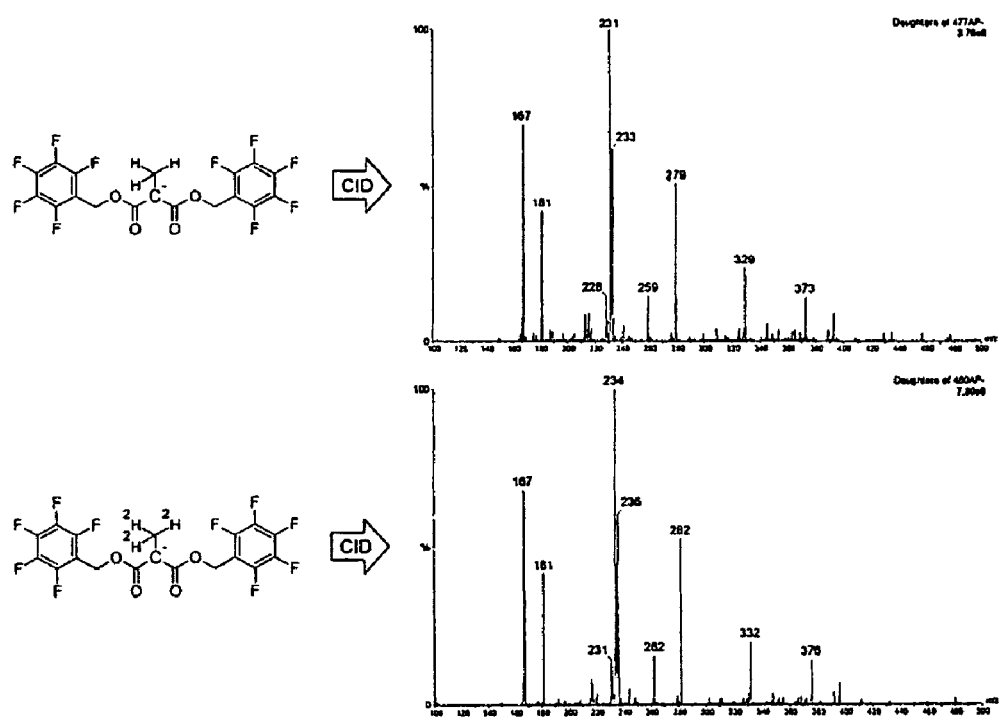
FIG. 5 shows dissociation mass spectra (daughter scan) of deprotonated MMA-PFB$_2$ (above) and MMA-d$_3$-PFB$_2$ (below) derivative by negative APCI.

The ion at m/z 477 was analyzed through MS/MS to check if it would produce ions useful for detection. The fragmentation spectrum of peak m/z 477 is shown in FIG. 5. Comparing the dissociation spectra from MMA-$PFB_2$ and MMA-$d_3$-$PFB_2$, it is observed at mass range above m/z 200, a mass difference of 3 Th indicating the presence of methyl group on these fragments. The most intense fragment (m/z 231) was chosen for a mass transition for quantification. Other mass transition (477>279) was selected as qualitative transition to establish ion ratios.

EXAMPLE 7

Optimization Studies for Extractive Alkylative Conditions

Figure 6:
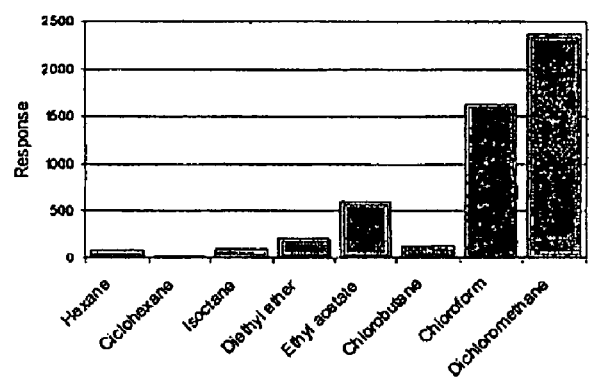
FIG. 6 shows the effect of different organic solvents on MMA-PFB$_2$ derivative yields.
Figure 7:
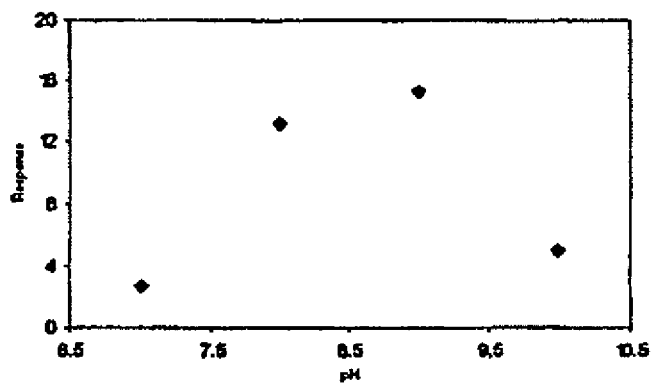
FIG. 7 shows the pH effect on relative yields of MMA-PFB$_2$ derivative.
Figure 8:
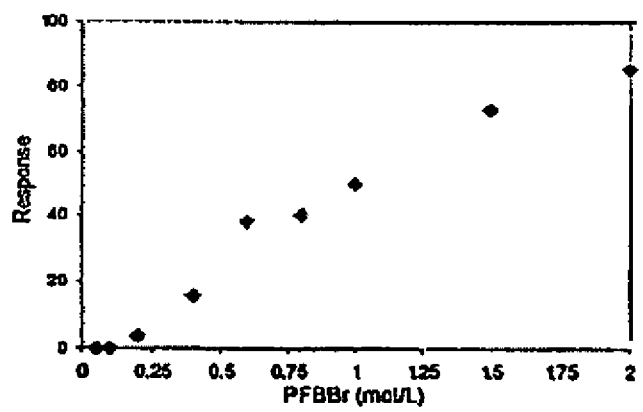
FIG. 8 shows the effect of alkylative agent concentration on relative yields of MMA-PFB$_2$ derivative.
Figure 9:
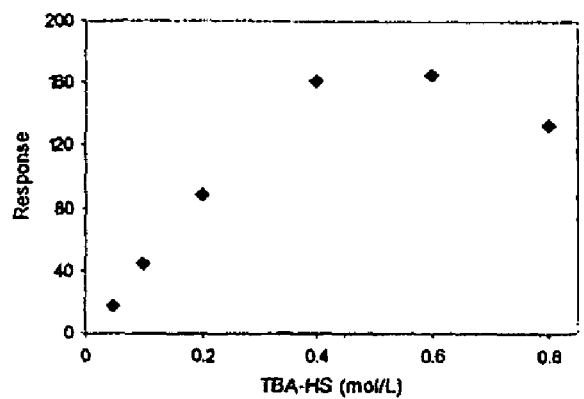
FIG. 9 shows the effect of phase transference agent concentration on relative yields of MMA-PFB$_2$ derivative.
Figure 10:
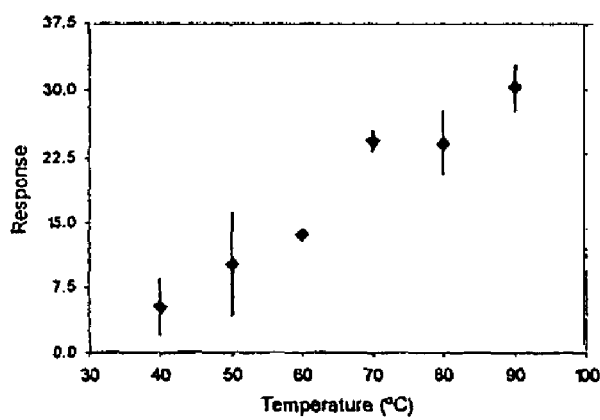
FIG. 10 shows the effect of reaction temperature on relative yields of MMA-PFB$_2$ derivative.

Higher yield of generation of MMA disubstituted derivative by PFBBr was obtained using dichloromethane solvent as can be seen on FIG. 6. FIG. 7 shows the pH effect in the formation of MMA-$PFB_2$ derivative. The maximum yield is obtained with reaction on buffer of pH about 9. As we can see from FIG. 8, there is a direct relation between yield of MMA-$PFB_2$ derivative and the amount of the alkylative reagent. We verified that the concentration of 0.1 mol/L results in enough sensitivity required to detect endogenous concentrations of MMA. The ideal concentration of phase-transfer reagent was about 0.8 mol/L (FIG. 9). The effect of temperature reaction on the generation of MMA-$PFB_2$ derivative is shown on FIG. 10. It was verified a reaction yield increase with temperature increase. In spite of the low boiling temperature of dichloromethane, we verified that it is possible to use temperature of 85° C. with polypropylene flask with screw lid and rubber sealing ring. Upon adjusting reaction time to 1 hour, we get a high reaction yield and the dichloromethane volume concentration is about 10% of its original volume. The combination of this organic residue with DMSO allowed the direction injection of this extract on chromatographic method.

EXAMPLE 8

Chromatographic Method for Determination and Quantification by LC-MS/MS

Figure 11:
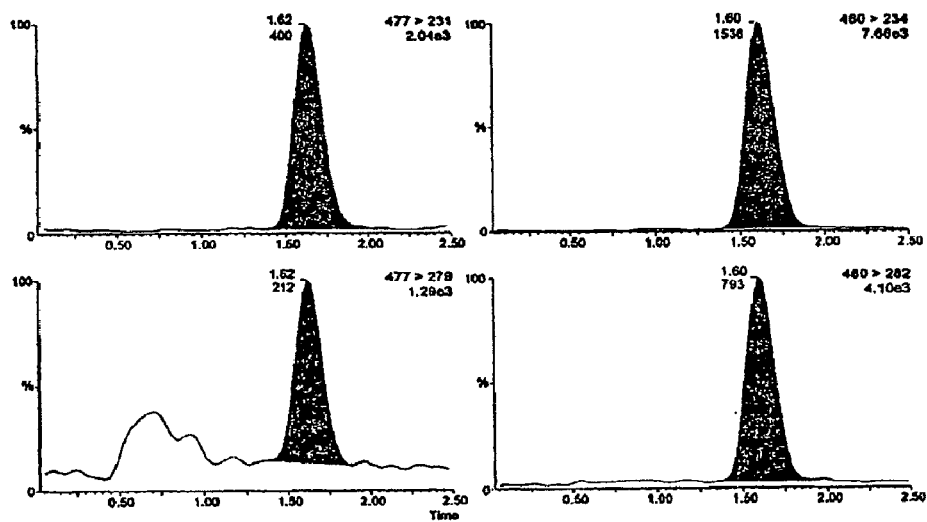
FIG. 11 represents typical chromatographic profile of serum sample analysis.
Figure 12:
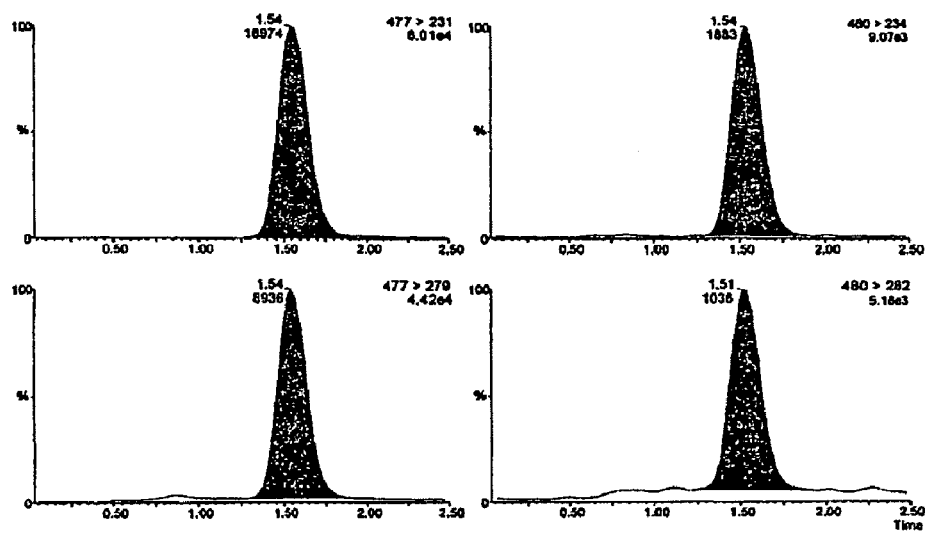
FIG. 12 represents typical chromatographic profile of urine sample analysis.
Figure 13:
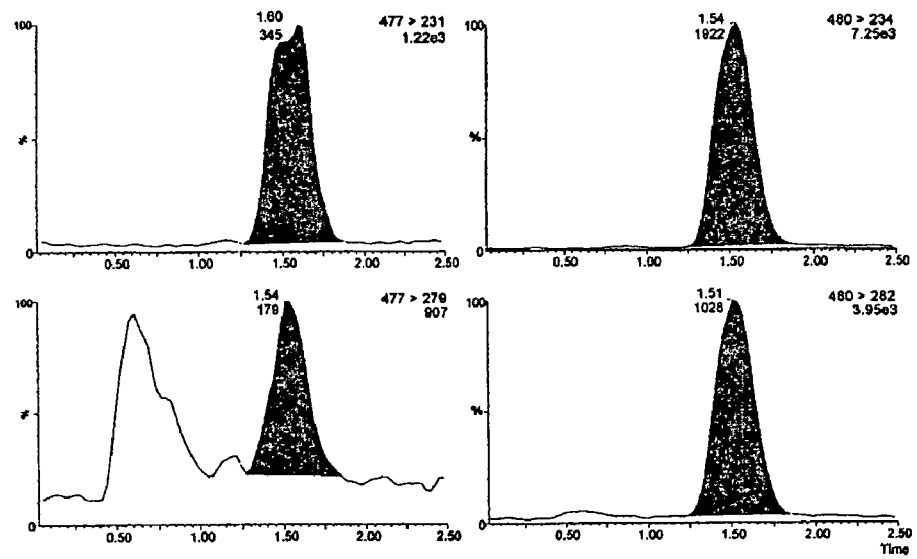
FIG. 13 represents typical chromatographic profile of liquor sample analysis.
Figure 14:
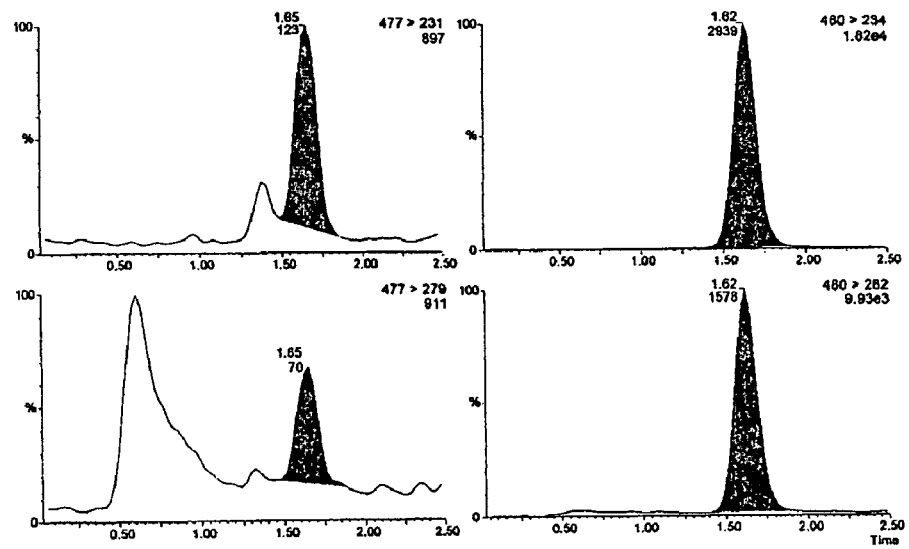
FIG. 14 represents typical chromatographic profile of total blood analysis on paper-filter.

Due to the high detection selectivity of tandem mass spectrometry through multiple reactions monitoring mode, the chromatographic profile of analysis of organic profile of serum samples is very simple, showing only one peak corresponding to MMA-$PFB_2$ derivative (FIG. 11). The use of 5 cm chromatographic column allowed a chromatographic analysis in 2.5 minutes. Since the injected extract has a large excess of reagents, it is important the retention of the analytes for 1-2 minutes to allow the elution of the excess of the reagents and DMSO, avoiding the suppression of analyte signal. Besides serum, the following matrixes were also tested: urine (FIG. 12), liquor (FIG. 13) and total blood on paper-filter (FIG. 14).

EXAMPLE 9

Method Analytical Validation

The assay accuracy was determined through EP5 protocol of "Clinical and Laboratory Standards Institute". Two 'pools' of 5 mL serum samples were prepared and to the second one, 42 μL of a sample of patient with methylmalonic acidemia whose MMA concentration was 180 μmol/L was added, in order to get a final concentration of 1.5 μmol/L. 50 μl aliquots of two levels were prepared and stored at −20° C. until the analysis preparation. The samples were analyzed in duplicate and through two daily analyses along 10 days. The data was analyzed with aid of EP Evaluator 4.0 program (David G. Rhoads Associates, Inc. Kennett Square, Pa.). The data obtained on the validation tests are summarized on table 3.

TABLE 3

Method analytical validation data

| | | | |
|---|---|---|---|
| Total imprecision | Concentrations (μmol/L) | 0.50 | 2.15 |
| (% CV) | (% CV) | 7.0 | 4.8 |
| Limits of | Concentrations (μmol/L) | 0.08 | |
| quantitation | (% CV) | 17.6 | |
| Accuracy | Concentrations (μmol/L) | 0.80 | 11.25 |
| | % | 2.1 | 1.8 |
| Linearity | | Até | |
| | Concentrations (μmol/L) | 180.00 | |
| | Allowed systematic error (%) | 10.0 | |
| Recovery | (%) | 104.1 | |

The linearity and recovery for the method were checked analyzing in triplicate 11 samples produced through serial dilutions of one sample of 180 μmol/L concentration with a pool of dialyzed serum (final concentrations of 180.00, 90.00, 45.00, 22.50, 11.25, 5.62, 2.80, 1.60, 0.80, 0.40 and 0.20 μmol/L). Data were analyzed with "Accuracy and Linearity" module of EP Evaluator 4.0 program using a 10% allowed systematic error.

The quantification limit for the method was determined through the analysis of three samples of low values (0.15, 0.12 and 0.08 μmol/L) along 10 days. The quantification limit was determined as the lowest concentration, which shows a coefficient of variation inferior to 20%. Data were analyzed with "Sensitivity by Limits of Quantification" module of EP Evaluator 4.0 program.

The limits of quantification verified for the method was 0.08 μmol/L with coefficient of variation of 17.6%. The method imprecision was assessed through the analysis of two concentrations (0.50 and 2.15 μmol/L) in duplicate, in two runs per day, along 10 days. Coefficients of variation of 7.0 and 4.8%, respectively, were verified. The linearity was verified in the interval of 0.20-180.00 μmol/L. The same test checked the method recovery, which was appropriate.

Figure 15:
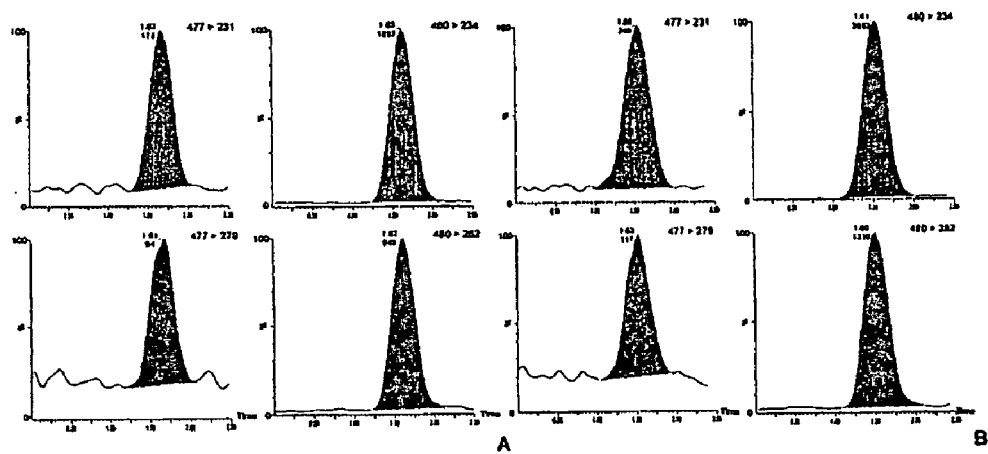
FIG. 15 shows the assessment of possible interference caused by succinic acid. A: pool of serum (MMA concentration=0.12±0.01 mmol/l; ion ratio=2.0±0.1). B: 'pool' of serum added of 1000 mmol/L of succinic acid (MMA concentration=0.13±0.01 mmol/l; ionic ratio—2.1±0.1).

The interferent tests were performed adding concentration of 1.00 mmol/L succinic acid to a 'pool' and comparing the concentrations and the qualitative ionic rates obtained from MMA on the sample with or without the interferent addition. The comparison between the concentration and 'ion ratio' shown in the sample with or without succinic acid addition has proved the total absence of interference (FIG. 15).

Figure 16:
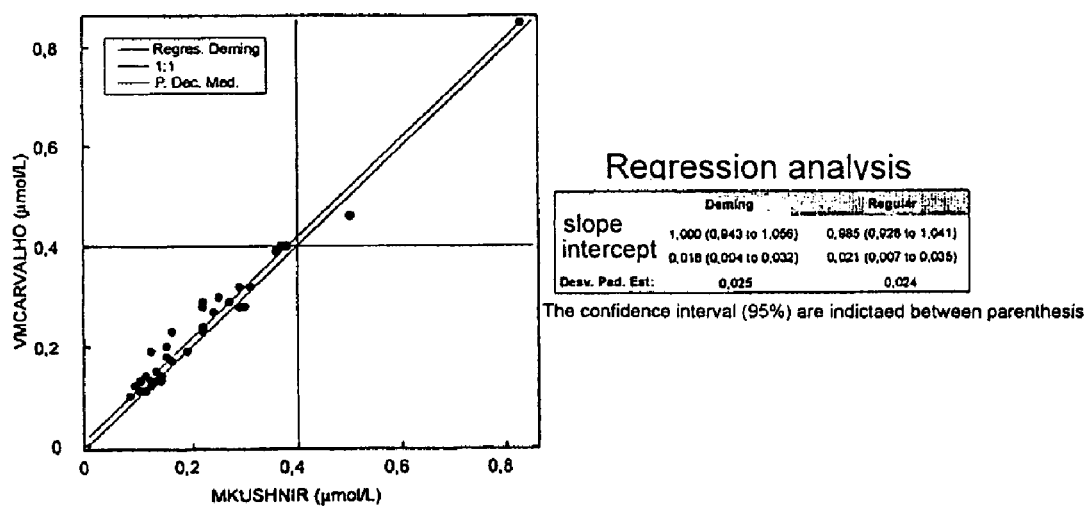
FIG. 16 shows the method accuracy through comparison with other one described on literature.

The method precision was verified through the analysis of comparative analysis of forty serum samples by the present method and the one described by Kushnir et al[11] as presented on FIG. 16. Linear regression obtained by Deming method showed a 1.000 slope, confirming that the method has high accuracy compared to other described in the literature.

EXAMPLE 10

Typical Analysis Procedure

The methodology used to carry out the present invention follows, in a non limitation way, subsequent steps, which can be properly adjusted to several needs of different industrial sectors, which use MMA quantification. As an example, we can exemplify that the present invention starts by the samples collection on appropriate tubes. These samples will be stored in order to separate the phase that has MMA, which will be analyzed, from other impurities. In the case of serum, as a sample, it will be centrifuged. After centrifugation, the samples, calibration and quality control standards are stored in the freezer; the samples, calibration and quality control standards are transferred to appropriate tubes; a solution of deuterium internal standard is added to each tube; a phase transference reagent solution is added to each tube; a derivatizing agent solution is added to each tube; the mixture is placed on stirring equipment with heating; the mixture is incubated in an appropriate time to obtain the highest yield of the PFB derivative; the tubes are centrifuged for phases separation; the organic phase is transferred to chromatographic vials; preferably 50 μl of organic phase is injected into the chromatographic system and the samples are quantified through appropriate software for this purpose.

The description above of the present invention was shown for illustration and description. Besides that, the description does not intend to limit the invention to the form present herein. Consequently, variations and modifications compatible to the herein above teaching and the ability or knowledge of relevant technique, are within the scope of the present invention.

The embodiments shown above tend to better explain the ways known for invention practice and allow the technicians of the area to use the invention in such or others, embodiments and with several necessary modifications by the specific applications or uses of the present invention. It is the purpose that the present invention includes all its modifications and variations, within the scope described in the specification and appended claims.

EXAMPLE 11

BIBLIOGRAPHY

1—Kovachy, R. J., Allen, R. H. 1983. Recognition, Isolation, and Characterization of Rat Liver D-Methylmalonyl Coenzyme A Hydrolase. The Journal of Biological Chemistry. 258:11415-11421.

2—Fenton, W. A., Rosenberg, L. E. 2001. Disorders of propionate and methylmalonate metabolism. In: Scriver, C. R., Beaudet, A. L., Sly, W. S., Valle, D., eds. The metabolic and molecular bases of inherited disease, 8th ed. New York: McGraw-Hill, 2001:2177-93.

3—Bashir, H. v., Hinterberger, H., Jones, B. P. 1996. Methylmalonic acid excretion in vitamin B12 deficiency. British Journal of Haematology. 12:704-11.

4—Barness, L. A., Young, D., Mellman, W. J., Kahn, S. B., Williams, W. J. 1963. Methylmalonate excretion in a patient with pernicious anemia. New England Journal of Medicine. 268:144-6.

5—HØLLELAND, G., Schneede, J., Ueland, P. M., Lund, P. K., Refsum, H., Sandberg, S. 1999. Cobalamin deficiency in general practice. Assessment of the diagnostic utility and cost-benefit analysis of methylmalonic acid determination in relation to current diagnostic strategies. Clinical Chemistry. 45:189-98.

6—Norman, L. I., Berry, H. K., Denton, M. D. 1979. Identification and quantitation of urinary dicarboxylic acids as their dicyclohexyl esters in disease states by gas chromatography mass spectrometry. Biological Mass Spectrometry. 6:546-553

7—Husek, P. 1995. Simultaneous prolife analysis of plasma amino and organic acids by capillary gas chromatography. Journal of Chromatography B: Biomedical Applications. 669:352-357.

8—Stabler, S. P., Marcell, P. D., Podell, E. R., Allen, R. H., Lindenbaum, J. 1986. Assay of methylmalonic acid in the serum of patients with cobalamin deficiency using capillary gas chromatography-mass spectrometry. The Journal of Clinical Investigation. 77:1606-1612.

9—Rasmussen, K. 1989. Solid-phase sample extraction for rapid determination of methylmalonic acid in serum to and urine by a stable-isotope-dilution method. Clinical Chemistry. 35:260-264.

10—Magera, M. J., Helgeson, J. K., Matern, D., Rinaldo, p. 2000. Methylmalonic acid measured in plasma and urine by stable-isotope dilution and electrospray tandem mass spectrometry. Clinical Chemistry, 46:1804-10

11—Kushnir, M. M., Komaromy-Hiller, G., Shushan, B., Urry, F. M., Roberts, W. L. 2001. Analysis of dicarboxylic acids by tandem mass spectrometry. High-throughput quantitative measurement of methylmalonic acid in serum, plasma, and urine. Clinical Chemistry. 47:1993-2002.

The invention claimed is:

1. A method of determining the presence of methylmalonic acid in a biological sample, comprising:
   (a) extracting methylmalonic acid from the biological sample and derivatizing the extract with pentafluorobenzyl bromide;
   (b) subjecting the sample to negative mode atmospheric pressure chemical ionization;
   (c) detecting an ion having a mass-to-charge ratio (m/z) of 477 using mass spectrometry.

2. The method of claim 1, wherein the biological sample is selected from the group consisting of a serum sample, a urine sample, a whole blood sample, a cerebrospinal fluid sample and a saliva sample.

3. The method of claim 2, further comprising detecting fragment ions having a mass-to-charge ratios (m/z) of 231 and 279 using a tandem mass spectrometry.

4. The method of claim 3, wherein the concentration of methylmalonic acid is determined using a deuterated internal standard.

5. A method of determining the presence of methylmalonic acid in a biological sample according to claim 1, comprising:
   a) obtaining a biological sample from a subject;
   b) transferring a small volume of the biological sample to a screw-cap tube;
   c) adding a deuterated internal standard solution to the tube;
   d) adding an alkalinizing buffer with a phase-transfer reagent to the tube;
   e) adding a derivatizing solution in an organic solvent to the tube;
   f) stirring the biological sample and added reagents mixture with heating for a period of time long enough to reach a high yield for the derivatization reaction;
   g) centrifuging the mixture for phase separation;
   h) injecting an organic phase onto a chromatographic system; and
   i) detecting methylmalonic acid through mass spectrometry with negative mode atmospheric pressure chemical ionization.

6. The method of claim 5, wherein the volume of the biological sample in (b) is 50 microliters.

* * * * *